(12) United States Patent
Flanagan et al.

(10) Patent No.: US 9,610,150 B2
(45) Date of Patent: Apr. 4, 2017

(54) DEVICES FOR SIZING A CAVITY TO FIT AN ORGAN AND RELATED METHODS OF USE

(71) Applicant: Boston Scientific Scimed, Inc., Maple Grove, MN (US)

(72) Inventors: Aiden Flanagan, Kilcolgan (IE); Mark W. Boden, Harrisville, RI (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 50 days.

(21) Appl. No.: 14/558,171

(22) Filed: Dec. 2, 2014

(65) Prior Publication Data
US 2015/0265392 A1    Sep. 24, 2015

Related U.S. Application Data

(60) Provisional application No. 61/954,701, filed on Mar. 18, 2014.

(51) Int. Cl.
| | |
|---|---|
| *A61F 2/04* | (2013.01) |
| *A61B 17/00* | (2006.01) |
| *A61B 90/00* | (2016.01) |

(52) U.S. Cl.
CPC ...... *A61F 2/04* (2013.01); *A61B 2017/00809* (2013.01); *A61B 2090/063* (2016.02); *A61F 2002/043* (2013.01); *A61F 2210/0061* (2013.01); *A61F 2210/0085* (2013.01); *A61F 2250/001* (2013.01)

(58) Field of Classification Search
CPC .............. A61F 2/2481; A61F 2002/043; A61F 2210/0061; A61F 2210/0085; A61F 2250/001; A61F 2/04; A61F 2210/0004; A61B 2017/00809; A61B 2090/063
See application file for complete search history.

(56) References Cited

U.S. PATENT DOCUMENTS

| | | | | |
|---|---|---|---|---|
| 4,160,446 | A * | 7/1979 | Barrington | A61F 6/225 128/831 |
| 4,969,899 | A * | 11/1990 | Cox, Jr. | A61F 2/12 623/8 |
| 8,252,339 | B2 | 8/2012 | Figuly et al. | |
| 8,445,589 | B2 | 5/2013 | Ingenito et al. | |
| 2002/0165618 | A1 * | 11/2002 | Ingenito | A61F 2/0063 623/23.65 |

(Continued)

OTHER PUBLICATIONS

Chatila, Wissam M., Satoshi Furukawa, John P. Gaughan, and Gerard J. Criner. "Respiratory Failure After Lung Transplantation." Chest 123.1 (2003): 165-73.*

(Continued)

*Primary Examiner* — Charles A Marmor, II
*Assistant Examiner* — Thaddeus Cox
(74) *Attorney, Agent, or Firm* — Bookoff McAndrews, PLLC

(57) ABSTRACT

A method of sizing a cavity to fit an organ is disclosed. The method may include inserting the organ into the cavity. The method may also include inserting a support member into the cavity and inserting a substance into the cavity or the support member. The support member and the substance may at least partially fill a void space in the cavity after the organ is inserted therein.

14 Claims, 3 Drawing Sheets

(56) References Cited

U.S. PATENT DOCUMENTS

| | | | | |
|---|---|---|---|---|
| 2007/0073402 A1* | 3/2007 | Vresilovic | ............... | A61L 27/52 623/17.12 |
| 2007/0156113 A1* | 7/2007 | Macha | .................... | A61M 5/14 604/500 |
| 2008/0275295 A1* | 11/2008 | Gertner | ............ | A61B 17/00234 600/37 |
| 2008/0295829 A1* | 12/2008 | Evens | ....................... | A61F 2/00 128/202.27 |
| 2013/0046275 A1* | 2/2013 | Holzer | ................. | A61K 9/0024 604/500 |
| 2013/0280318 A1* | 10/2013 | Lu | ........................... | A61L 27/56 424/443 |
| 2015/0272591 A1* | 10/2015 | Folan | ............... | A61B 17/12181 623/23.7 |

OTHER PUBLICATIONS

Kozower et al., "Potential for detrimental hyperinflation after lung transplantation with application of negative pleural pressure to undersized lung grafts," The Journal of Thoracic and Cardiovascular Surgery, Feb. 2003, p. 430-432, retrieved on Oct. 6, 2016.*

* cited by examiner

DEVICES FOR SIZING A CAVITY TO FIT AN ORGAN AND RELATED METHODS OF USE

CROSS-REFERENCE TO RELATED APPLICATION

This patent application claims benefit of priority under 35 U.S.C. §119 to U.S. Provisional Patent Application No. 61/954,701, filed Mar. 18, 2014, the entirety of which is incorporated herein by reference.

DESCRIPTION OF THE DISCLOSURE

Field of the Disclosure

This disclosure relates generally to devices for sizing a cavity to fit an organ and related methods of use. More particularly, the disclosure relates to medical and surgical devices and related methods for sizing a pleural cavity to fit an organ (e.g., a lung) for treating a pulmonary system.

Background of the Disclosure

Organ transplantation surgery involves replacement of a diseased organ with a healthy organ from a donor. For example, a lung transplant may be prescribed to treat a number of diseases such as chronic obstructive pulmonary disease (COPD) (e.g., emphysema), idiopathic pulmonary fibrosis, cystic fibrosis, idiopathic pulmonary hypertension, alpha 1-antitrypsin deficiency, replacing previously transplanted lungs that have since failed, bronchiectasis and sarcoidosis, etc. In an instance, during one method of lung transplantation, a surgeon makes a cut in the chest and removes the diseased lung. The surgeon then implants the new lung by suturing together the main blood vessels and the air passage. One of the prominent requirements for lung transplant is size match, e.g., the donated lung should be of an appropriate size to fit within the recipient patient's chest cavity and should be of sufficient size to adequately oxygenate the patient. In some instances, the size of the donated lung may not match the size of the recipient patient's cavity. Even if the size of the donated lung is close to the required size, slight mismatches may lead to atelectasis and/or pneumothorax, further leading to increased complications and/or increased stay in an intensive care unit (ICU), or even death of the patient, among other complications.

Thus, there remains a need for methods and devices that allow for better cavity-to-organ size matching when performing an organ transplant.

SUMMARY OF THE DISCLOSURE

The present disclosure is directed to a method of sizing a cavity to fit an organ by inserting a support member into the cavity to improve the cavity's fit with the organ, when, e.g., the organ may be smaller than the cavity.

In one aspect of the disclosure, a method of sizing a cavity to fit an organ may include inserting a support member into the cavity, and inserting a substance into the cavity or the support member. The support member and the substance may at least partially fill a void space in the cavity.

In another embodiment, the method may include inserting a support member into a cavity in a first configuration and adjusting the size or shape of the support member to a second configuration. For example, the support member may be inserted into the cavity while disposed in a first size or shape, and may be capable of receiving a substance that expands the device to a second size or shape.

Various embodiments of the disclosure may also include one or more of the following aspects: wherein the support member may be inserted into the cavity in a collapsed configuration; wherein the organ may be a lung, and the cavity may be a chest cavity; wherein the support member may transmit a motion of the chest cavity to the lung via the substance; wherein the lung may not fill a portion of the chest cavity when the lung is fully expanded; wherein the substance may be a foaming polymer; wherein the substance may be an elastic polymer or gel; wherein the elastic polymer or gel may be a liquid at a first temperature, and may be a gel at a second temperature; wherein the second temperature may be a body temperature; wherein the organ may be a transplanted organ; and wherein the substance and the support member may remain in the cavity after an organ transplant procedure may be completed.

In another aspect, the present disclosure may be directed to a method of sizing a cavity to fit an organ. The method may include inserting a support member into the cavity and around the organ such that support member transmits a motion of the cavity wall to the organ.

Various embodiments of the present disclosure may also include one or more of the following aspects: wherein the support member may be a space occupying device; wherein the support member may be a mesh coupled to the organ; wherein the method may further include securing the mesh to the cavity; wherein securing the mesh to the cavity may include securing the mesh to tissue adjacent the cavity and other than the organ; and wherein the mesh may have a hardness that approximates the hardness of the organ.

In yet another aspect, the present disclosure may be directed to a method of sizing a chest cavity to fit an undersized lung. The chest cavity may provide a first volume, and the lung may occupy a second volume that is less than the first volume. The method may also include inserting a space occupying device into the chest cavity, and positioning the space occupying device adjacent the lung. The method may also include inserting a substance into the space occupying device to increase a volume of the space occupying device to a third volume that is defined by the difference between the first volume and the second volume.

Various embodiments of the disclosure may also include one or more of the following aspects: wherein the lung may not fill the first volume of the chest cavity when the lung is fully expanded; wherein the substance and the space occupying device may remain in the chest cavity after an organ transplant procedure is completed; wherein the undersized lung may have undergone a lung volume reduction procedure or may be a transplanted lung.

Additional characteristics, features, and advantages of the disclosed subject matter will be set forth in part in the description that follows, and in part will be apparent from the description, or may be learned by practicing the disclosure. The characteristics and features of the disclosure can be realized and attained by way of the elements and combinations particularly pointed out in the appended claims.

It is to be understood that both the foregoing general description and the following detailed description are exemplary and explanatory only, and are not restrictive of the disclosed subject matter.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made to certain exemplary embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. The term "proximal" refers to the end closest to the medical professional when placing a device in the patient.

Overview

Embodiments of the present disclosure relate to devices and methods configured for sizing a cavity to fit an organ. For example, embodiments of the disclosed devices and method(s) may be directed to sizing a chest cavity to fit a lung and/or improving the contact area between the chest wall and the lung for improved inflation and deflation mechanics.

Exemplary Embodiments

The embodiments disclosed herein include devices and methods for sizing a cavity to fit one or more lungs. However, it should be noted that the present disclosure contemplates use of the devices and methods for other bodily cavity filling applications, such as Pelvic Floor Repair, Hernia Repair, reconstructive surgery, cosmetic surgery, or the like, and in connection with other organs, including, e.g., kidneys, heart, liver, or the like.

Figure 1:
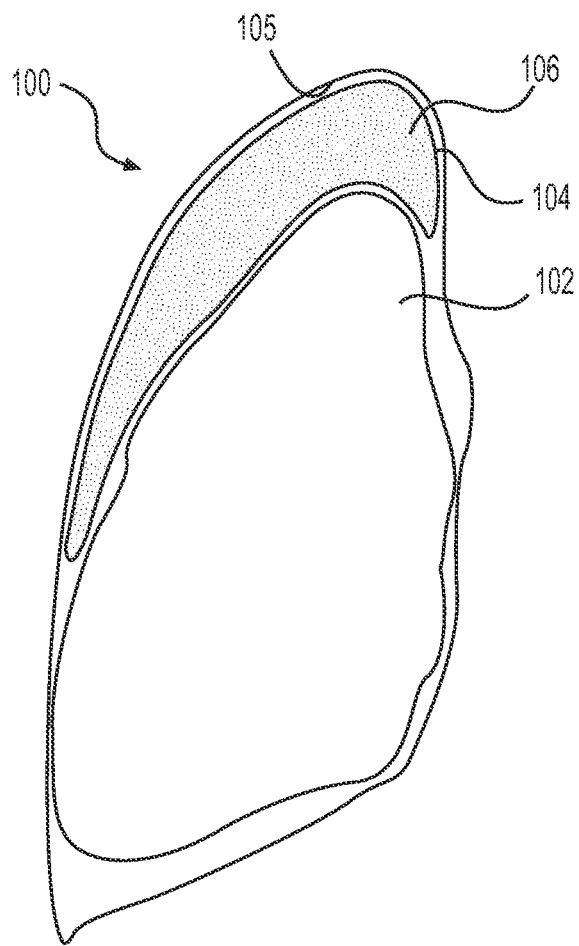
FIG. 1 is an in vivo illustration of an exemplary support member inserted into a chest cavity while in a first configuration, according to one embodiment of the present disclosure.

Lung transplantation typically involves replacing one or both diseased lungs with healthy lungs from a donor. During the operation, the surgeon may make a cut in the chest and may remove the diseased lung. The surgeon then may implant the new lung by sewing together or otherwise connecting the main blood vessels and air passages. In some instances, the size of the donated lung may not match the size of the chest cavity. For example, the donated lung may be too small for the recipient's chest cavity, causing a void or space to be left after implanting the donated lung. The void or space can cause several complications and/or negative effects, including full rejection of the implant. In particular, if the lungs are relatively small and do not completely fill the target cavity in the recipient patient, the lungs may not receive sufficient support from the surrounding chest cavity and/or may not receive sufficient assistance from muscular restriction and contraction during the breathing process. A support member, such as a space occupying device 104, may be implanted to fill the void in the chest cavity 100 after the lung is transplanted, as shown in FIG. 1, so as to improve the fit of the newly implanted lung.

In some embodiments, space occupying device 104 may be utilized in the lung cavities of patients having a portion of a lung removed, such as, e.g., in patients having a lobectomy due to bronchiectasis, cancer, emphysema, lung volume reduction surgery, fungal and/or other infections, cysts, among other conditions of the lung.

In an exemplary embodiment, a lung 102 may be implanted in a chest cavity 100 which is defined by a chest wall 105. The lung 102 may be a donated lung having a size less than the size of the chest cavity such that the lung 102 may not fill the entire volume of the chest cavity 100, thereby leaving a void between the lung 102 and the chest wall 105. Space occupying device 104 may be configured to occupy the void between the lung 102 and chest wall 105. Space occupying device 104 may spread out along the chest wall 105, contacting (e.g., mechanically) an inner surface of the chest wall 105 and the lung 102. As lung transplantation may be an open surgery, an empty (e.g., unfilled) space occupying device 104 can be pushed or otherwise inserted into the void between the lung 102 and chest wall 105. Once in place, the space occupying device 104 may be filled by injecting a substance 106 using any suitable introduction device, such as, e.g., sheaths, injectors, syringes, catheters, or the like. In some embodiments, a lumen of a catheter can be connected to the space occupying device 104 for introducing the substance 106. The catheter may be coupled (permanently or temporarily) to the space occupying device 104. As the substance 106 is injected, the substance 106 may flow into the space occupying device 104, causing substance 106 and space occupying device 104 to expand and conform to the shape of the space left between the chest cavity 100 and the lung 102 to achieve maximum surface area contact. Thus, the space left between the lung 102 and the chest wall 105 may be occupied by a filled space occupying device 104, allowing for mechanical forces to transmit between the chest wall 105 and the lung 102, either by direct contact between the lung 102 and chest wall 105 (which is promoted by the filled space occupying device 104) or via the substance 106 and space occupying device 104 themselves transmitting force therethrough.

Any suitable compressible or incompressible biocompatible substance including solids, gases, liquids, gels, microspheres or the like having flow properties already known in the art may be used to fill the space occupying device 104 depending on the application, desired force transmission, and desired support characteristics may be used. In some embodiments, the substance may have the same compliance as the lung. In some other embodiments, a foaming polymer such as polyurethane, starch, or the like may be used to fill the space occupying device 104. In some embodiments, the foaming polymer may be a liquid that may flow and conform to the shape of the chest cavity 100, thereby achieving maximum surface area contact between the space occupying device 104, chest wall 105, and lung 102. The foaming polymer may have a large void volume to enable compression and expansion which can be optimized to support the lung 102 during expansion and contraction, and to transmit force to the lung 102 from the chest wall 105. The foaming polymer may be flexible and elastomeric to allow space occupying device 104 to move as the lung 102 expands and contracts. In some other embodiments, a non-foam highly elastic polymer or gel, for example, a thermoresponsive gel such as matrigel or the like may be used to fill the space occupying device 104. Such polymer or gel may be liquid at lower temperatures and may become a gel when exposed to body temperature. In some embodiments, substance 106 may be formed of a biocompatible material for patient safety should any substance 106 escape space occupying device 104. In some embodiments, space occupying device 104 may itself be a foam, foaming polymer, active polymer, silicone, or a mechanical cage.

Figure 2:
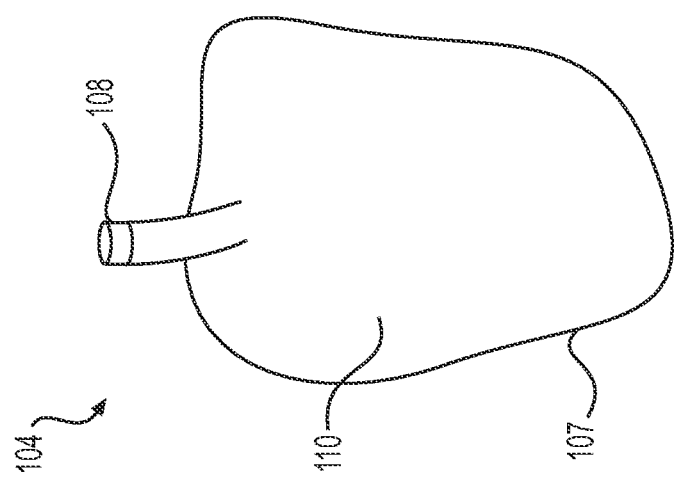
FIG. 2 is a front view of the exemplary support member of FIG. 1 in a second configuration.

The space occupying device 104 may be filled with the substance 106 through a nozzle 108, as shown in FIG. 2. The nozzle 108 may be provided as a valve to open and close the space occupying device 104, and can be formed as a mediator through which the space occupying device 104 may be filled. However, other suitable alternative nozzle and/or opening configurations are also contemplated. Referring to FIGS. 1 and 2, the substance 106 may fill volume 110 of the space occupying device 104 partially or wholly. In some embodiments, the substance 106 may fill volume 110 depending upon the dimensions of the space within the chest cavity 100 that need to be occupied. After filling the space occupying device 104 to a sufficient volume, the catheter (or delivery device) may be removed and the open end of the space occupying device 104 may be closed using methods that are known in the art such as welding, suturing, sealing, or the like. In some embodiments, the space occupying device 104 and the substance 106 may remain in the chest cavity 100 after an organ transplant procedure is completed. Space occupying device 104 and/or substance 106 may include radiopaque markers to facilitate imaging and proper fitting.

As shown in FIG. 2, the space occupying device 104 may be defined by an outer wall or membrane 107. The nozzle 108 may be disposed at any suitable location (e.g., an end) of the space occupying device 104, thereby allowing the fluid or substance to ingress. The membrane 107 may be formed from a thin elastic membrane of a biocompatible material, for example, poly(Styrene-block-IsoButylene-block-Styrene) (SIBS), polyisobutylene polyurethane (PIB-PUR), silicone rubber, nitrile rubber, neoprene, ethylene-propylene-diene rubbers, styrene-butadiene, Viton and other fluoropolymer elastomers, polyisoprene, polyurethanes, among others. In some embodiments, membrane 107 may be formed from non-elastic membranes, such as, e.g., polyethylene, polyethylene terephthalate, polypropylene, polyesters, acrylic polymers, or the like. The membrane 107 may be formed by various methods, including, but not limited to, injection molding, blow molding, electrospinning, dip coating, spray coating over a mandrel, or the like. In some embodiments, the outer surface of space occupying device 104 may be textured to improve tissue incorporation and better apposition to the organ and cavity. The membrane 107 may conform to the shape of the chest cavity 100 as the membrane 107 is filled with the substance 106, thereby achieving the high contact surface area. Because of the high contact surface area, the membrane 107 surrounding the injected substance 106 may transmit the motion of the chest wall during breathing to the lung 102, thereby causing the lung 102 to expand and inflate according to a normal healthy motion of the lung. Various other support members may be used to replace the space occupying device 104, including space occupying devices of different shapes (e.g., square, tubular, S-shaped, circular, non-symmetrical, or the like), support members configured as netting, support members configured as a single piece elastic material, space occupying devices that are self-closing and do not include a nozzle, among others. The various support members may function in a substantially similar manner as described with reference to space occupying device 104.

Membrane 107 may be configured to expand more easily in one direction than in others to achieve a desired final expanded shape. In one embodiment, membrane 107 may easily expand on a first pair of the sides, while maintaining a flattened shape on, e.g., the top and bottom sides. The variability in expansion may be achieved using different materials, orientations, and/or thicknesses. In some embodiments, space occupying device 104 may have multiple chambers in order to influence final shape and performance of space occupying device 104. The presence of multiple chambers may be particularly useful when substance 106 is a liquid or gas.

In some embodiments, space occupying device 104, substance 106, and membrane 107 may be formed from one or more degradable materials that would degrade over time and are replaced by acellular material such as collagen. In some embodiments, membrane 107 may include one or more of polyester elastomers (e.g., polyglycolide-co-caprolactone, plga, or crosslinked plga), degradable urethanes, among others. In some embodiments, substance 106 may include one or more of foaming polyurethanes, hydrogel beads, or the like.

In some embodiments, one or more of space occupying device 104, substance 106, and membrane 107 may include one or more agents, such as, e.g., hemostatics, adhesive peptides, anti-inflammatory drugs, anti-proliferative agents to reduce scarring, growth factors, among others.

Figure 3:
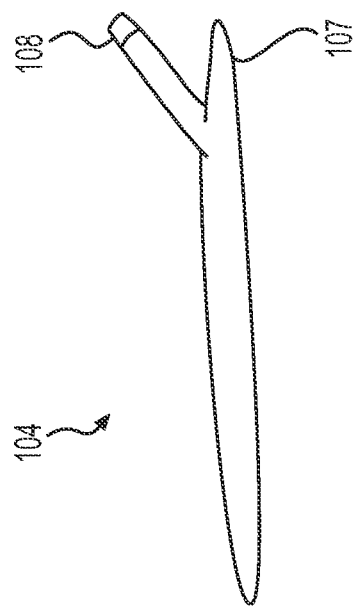
FIG. 3 is a side view of the exemplary support member of FIG. 1 in a second configuration.

FIG. 3 is a side view of an empty space occupying device in a second (or collapsed) configuration. The space occupying device 104 may be empty while being inserted into the chest cavity 100. Alternatively, the space occupying device 104 may be delivered to the chest cavity 100 in a first (or expanded) configuration. Substance 106 may be delivered before, after, or during implantation of the space occupying device 104. In addition, substance 106 may be delivered into chest cavity 100 via any suitable devices and methods. For example, if the space occupying device 104 is formed from a self-healing, self-setting, or self-curing material, the substance 106 could be delivered by syringe. In one embodiment, nozzle 108 may be a septum or one-way valve configured to allow delivery of substance 106 into space occupying device 104, via, e.g., a syringe or the like. In addition, the amount of substance 106 can be easily adjusted before, during, or after the implant procedure. For example, if after the initial implant procedure, a medical professional notes that the lung 102 is not fully supported within (e.g., is too small for) the chest cavity 100 (through the use of x-ray, CAT-scan, magnetic imaging, sonar, ultrasound, other imaging systems, laparoscopic surgery, robotic surgery, open surgery, etc.) the medical professional can access the space occupying device 104 to insert an additional amount of substance 106 (or, alternatively, remove substance 106). The insertion/removal of substance 106 can be accomplished by inserting a catheter, cannula, or similar device into the space occupying device 104, and then injecting/removing the substance 106 and removing the cannula from the space occupying device 104 and the patient. Alternatively, a port or stoma (not shown) can be created in the patient during the initial implantation procedure, and the nozzle 108 or other access structure can extend out of the port or stoma for access after the initial implantation procedure. Thus, substance 106 can be easily added or removed from the space occupying device 104 after the initial implantation procedure based on patient observation. Access to the space occupying device 104 also can be accomplished by various surgical or medical procedures after initial implantation. For example, laparoscopic, robotic, and open surgery techniques could provide access to the space occupying device 104 after initial implantation in order to monitor, refill, or remove substance from the space occupying device 104.

Figure 4:
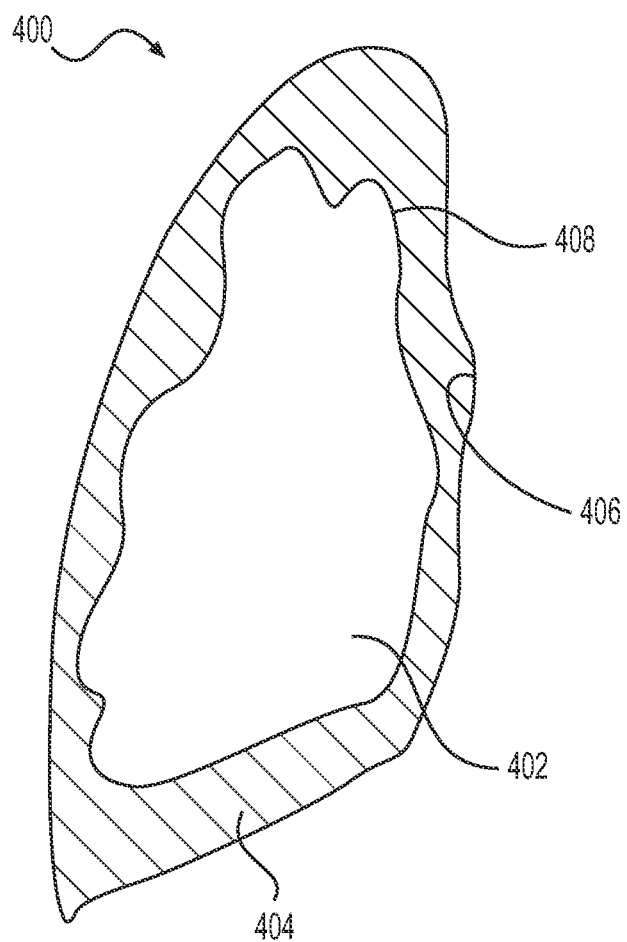
FIG. 4 is an in vivo illustration of a support member, according to another embodiment of the present disclosure.

FIG. 4 is an in vivo view illustration of another exemplary support member configured to support a lung in a chest cavity. In this embodiment, a chest cavity 400 may include an undersized lung 402 implanted therein. The support member can be configured as a mesh 404 and may be inserted into the chest cavity 400 to support the lung 402.

The mesh 404 may be implanted around or otherwise coupled to undersized lung 402 to couple lung 402 to an inner surface 406 of chest cavity 400. Thus, the mesh 404 may be attached to an inner surface 406 of the chest cavity 400. For example, the mesh 404 can be attached to an inner surface 406 (which could include, e.g., ribs, ligaments, or other suitable tissue) by suturing, adhesives, friction fit, or other attachment mechanisms. In some embodiments, the mesh 404 may be wrapped snuggly around an outer surface 408 of the lung 402. In some embodiments, the mesh 404 may be sutured or stapled with the inner surface 406 of the chest cavity 400. Mesh 404 may be coupled to lung 402 by any suitable mechanism, such as, e.g., suturing, adhesives, and the like. Mesh 404 may surround an entirety of lung 402, or may alternatively only surround a portion of lung 402, if desired.

The mesh 404 may be flexible enough to allow expansion and contraction of the lung 402 during breathing. Thus, the mesh 404 may have a Young's modulus of elasticity that is optimized to allow for lung expansion while facilitating back and forth movement of the lung 402. In some embodiments, the mesh 404 may include a number of interconnected strands, such that pores or cells are formed in the strands, and the strands can be arranged in a matrix form. In some embodiments, the strands are knitted or woven in a direction such that motion of the mesh 404 with respect to the motion of the lung 402 is controlled by the knitting direction. For example, during expansion and contraction of the lung 402, the mesh 404 may be configured to move accordingly in a particular direction depending upon the direction of knitted strands. In some embodiments, the mesh 404 may be braided, woven, knitted, cut from sheet stock, or the like. The strands of the mesh 404 may be welded, molded, soldered to form the mesh 404. Mesh 404 may have different moduli in different locations depending on where support to the lung is required. In some embodiments, mesh 404 may be non-compliant on a first pair of surfaces (e.g., on a pair of side surfaces), and compliant on a second pair of surfaces (e.g., the top and bottom surfaces), or vice versa. In other embodiments, mesh 404 may have varying degrees of compliance along multiple surfaces. Mesh 404 may be flexible in one dimension, but not in another direction, e.g., mesh 404 may stretch in a vertical direction, but not in a horizontal direction. Mesh 404 may be made from multiple layers of overlapping materials. The overlapping materials may be arranged to be perpendicular to control the direction of deposition of extracellular matrix and/or cell alignment.

Materials used for the mesh 404 may be chosen from any elastomeric and/or biocompatible material. Examples of such materials may include, but are not limited to, polymers, such as, polyester, silk, nylon, natural rubbers, butadiene polymers and copolymers, styrenic polymers and copolymers, polyurethanes, polyurethane carbonates, polyureas, or the like; and natural grafts, such as, porcine dermis, small intestinal submucosa, or the like. The polymers may be biostable, or bioabsorbable. The composition of the polymers may be of a single polymer type, copolymers, including random or block copolymers, or another suitable polymer type. Alternatively or additionally, mesh 404 may include star polymers, polymer brushes, crosslinked polymers, or the like. Mesh 404 may include one or more of the elastic or non-elastic materials described above with reference to membrane 107. In some embodiments, the mesh may be made from a monofilament macroporous polypropylene. In other embodiments, the mesh 404 may be made from a plastic material, or combination of materials.

Embodiments of the present disclosure may be used in many different medical or non-medical environments. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A method of sizing a cavity to fit a lung, the method comprising:
    inserting a biodegradable support member into the cavity and in contact with the lung; and
    inserting a biodegradable substance into the biodegradable support member, wherein the biodegradable support member and the biodegradable substance at least partially fill a void space in the cavity, and the biodegradable substance includes biodegradable foaming polyurethane or biodegradable hydrogel beads.

2. The method of claim 1, wherein the biodegradable support member is inserted into the cavity in a collapsed configuration.

3. The method of claim 1, wherein the cavity is a chest cavity.

4. The method of claim 3, wherein the biodegradable support member transmits a motion of a wall surrounding the chest cavity to the lung via the biodegradable substance.

5. The method of claim 4, wherein the biodegradable support member is configured to degrade and be replaced by acellular material that transmits a motion of the wall surrounding the cavity to the lung.

6. The method of claim 3, wherein the lung does not fill a portion of the chest cavity when the lung is fully expanded.

7. The method of claim 1, wherein the lung is a transplanted lung.

8. The method of claim 1, wherein the biodegradable substance and the biodegradable support member remain in the cavity after a lung transplant procedure is completed.

9. The method of claim 1, wherein the biodegradable support member includes an elastomer, polyglycolide-co-caprolactone, plga, crosslinked plga, or urethane.

10. A method of sizing a chest cavity to fit an undersized transplanted lung during a lung transplant procedure, the chest cavity providing a first volume and the lung occupying a second volume that is less than the first volume, the method comprising:
    after the undersized transplanted lung is inserted into the chest cavity, inserting a biodegradable space occupying device into the chest cavity;
    positioning the biodegradable space occupying device adjacent to and in contact with the undersized transplanted lung; and
    inserting biodegradable foaming polyurethane or biodegradable hydrogel beads into the biodegradable space occupying device to increase a volume of the biodegradable space occupying device to a third volume that is defined by the difference between the first volume and the second volume, wherein the biodegradable space occupying device, and the biodegradable foaming polyurethane or biodegradable hydrogel beads, are configured to degrade and be replaced by acellular material that transmits a motion of a wall surrounding the chest cavity to the transplanted lung after completion of the lung transplant procedure.

11. The method of claim 10, wherein the biodegradable foaming polyurethane or biodegradable hydrogel beads, and the biodegradable space occupying device remain in the chest cavity after the lung transplant procedure is completed.

12. The method of claim 11, wherein the lung does not fill the first volume of the chest cavity when the undersized transplanted lung is fully expanded.

13. The method of claim 12, wherein inserting biodegradable foaming polyurethane or biodegradable hydrogel beads into the biodegradable space occupying device is via a syringe.

14. The method of claim 13, wherein the biodegradable support member includes an elastomer, polyglycolide-co-caprolactone, plga, crosslinked plga, or urethane.

* * * * *